US00PP07842P

United States Patent [19]

VandenBerg

[11] Patent Number: Plant 7,842

[45] Date of Patent: Mar. 24, 1992

[54] CHRYSANTHEMUM PLANT NAMED DARK POMONA

[75] Inventor: Cornelis P. VandenBerg, Salinas, Calif.

[73] Assignee: Yoder Brothers, Inc., Barberton, Ohio

[21] Appl. No.: 571,515

[22] Filed: Aug. 23, 1990

[51] Int. Cl.[5] ..... A01H 5/00

[52] U.S. Cl. ..... Plt./76

[58] Field of Search ..... Plt./79, 80, 81, 82, Plt./76

[56] References Cited

U.S. PATENT DOCUMENTS

P.P. 6,802 5/1989 VandenBerg ..... Plt. 80

4,616,099 10/1986 Sparkes ..... 47/58

OTHER PUBLICATIONS

Broertjes et al., 1980, A Mutant of a Mutant of a Mutant of a . . . Irradiation of Progressive Radiation-Induced Mutants in a Mutation-Breeding Programme with *Chrysanthemum morifolium*, Euphytica (29):525-530.

Broertjes et al., 1978, "*Applications of Mutation Breeding Methods in the Improvement of Vegetatively Propagated Crops*", Elsevier Sci. Pub. Co., N.Y., pp. 162-175.

Broertjes, 1966, Mutation Breeding of Chrysanthemums, Euphytica (15):156-162.

Gosling, ed., 6th ed., 1979, "*The Chrysanthemum Manual of the National Chrysanthemum Soceity*", Essex Telegraph Ltd., Colchester, England, pp. 329-336.

Searle et al., 1968, "*Chrysanthemums the Year Round*", Blandford Press, Ltd., London, England, pp. 27-29, 321-327.

Chan, 1966, Chrysanthemum and Rose Mutations Induced by X-Rays, Am. Soc. Hort. Sci., vol. 88, pp. 613-620.

Dowrick et al., 1966, The Induction of Mutations in Chrysanthemums Using X- and Gamma Radiation, Euphytica (15):204-210.

*Primary Examiner*—Howard J. Locker

*Attorney, Agent, or Firm*—Foley & Lardner

[57] ABSTRACT

A Chrysanthemum plant named Dark Pomona particularly characterized by its flat capitulum form; decorative capitulum type; dark purple ray floret color; diameter across face of capitulum of 121 to 127 mm. when fully opened when grown as a pinched disbudded pot mum; photoperiodic response to short days of 51 to 56 days; plant height of 20 to 30 cm. when grown as a pinched pot mum; recommended both as disbudded and spray pot mum; and spreading and prolific branching pattern, with 5 to 6 breaks per plant after pinch.

1 Drawing Sheet

The present invention comprises a new and distinct cultivar of Chrysanthemum, botanically known as *Dendranthema grandiflora*, and referred to by the cultivar name Dark Pomona.

Dark Pomona, identified as 81-893C19, is a product of a mutation induction program which had the objective of creating new Chrysanthemum cultivars that would expand the color range of an existing cultivar while retaining all other traits.

Dark Pomona was discovered and selected by Cornelis P. VandenBerg in a controlled environment in Salinas, Calif. in comparative flower trails of selections of radiation sports originating from irradiation of the cultivar identified as Pomona, disclosed in U.S. Plant Pat. No. 6,802. One selection in these flower trails was identified by the code number 6117, which was selected in May 1987 as one flowering plant within a flowering block established as rooted cuttings from stock plants of Pomona which had been exposed as unrooted cuttings to an X-ray source of 1750 rads. Repeated flowerings of 6117, which was originally selected as a bronze color mutation, showed a mixture of a bronze and a dark purple color sport. One plant of each color was reselected in January of 1988 and given the code numbers 4023 (81-893C19) and 4026 (81-893D19). In the final selection process code 4023 was selected as Dark Pomona, while 4026 was discarded from the program in July 1990.

The first act of asexual reproduction of Dark Pomona was accomplished when vegetative cuttings were taken from the initial selection in March 1988 in a controlled environment in Salinas, Calif., by technicians working under the supervision of Cornelis P. VandenBerg.

Horticultural examination of controlled flowerings of successive plantings has shown that the unique combination of characteristics as herein disclosed for Dark Ponona are firmly fixed and are retained through successive generations of asexual reproduction.

Dark Pomona has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice.

The following traits have been repeatedly observed and are determined to be basic characteristics of Dark Pomona, which, in combination, distinguish this Chrysanthemum as a new and distinct cultivar:

1. Flat capitulum form.
2. Decorative capitulum type.
3. Dark purple ray floret color.
4. Diameter across face of capitulum of 121 to 127 mm. when fully opened, when grown as a pinched disbudded pot mum.
5. Photoperiodic flowering response to short days of 51 to 56 days.
6. Plant height; with 15 long days after sticking unrooted cuttings, and with 1 to 3 applications of 2500 ppm B-9 SP, ranges from 20 to 30 cm. when grown as a pinched pot mum with 4 cuttings in a 15 cm. pot.

7. Recommended both as disbedded and spray pot mum.

8. Branching pattern is spreading and prolific, each plant having 5 to 6 laterals after pinch.

The accompanying photographic drawing is a color photograph of Dark Pomona grown as a pinched spray pot mum with 4 cuttings in a 15 cm. pot.

Of the commercial cultivars known to the inventor, the most similar in comparison to Dark Pomona is the parent cultivar Pomona. The most significant difference between Pomona and Dark Pomona is the ray floret color, with the color of Dark Pomona (70A to 71B) being significantly darker than the color of Pomona (74C). In addition, Dark Pomona has a slightly smaller diameter of capitulum by 6 mm., and has shown slightly less vigor by 1.5 to 2.5 cm. Under high light and high temperature summer conditions Dark Pomona has a much better color retention than Pomona.

In the following description color references are made to The Royal Horticultural Society Colour Chart. The color values were determined on plant material grown as a pinched spray pot mum in Salinas, Calif. on May 2, 1990.

Classification:

*Botanical.*—*Dendranthema grandiflora* cv Dark Pomona.

*Commercial.*—Decorative disbud and spray pot mum.

INFLORESCENCE

A. Capitulum:

*Form.*—Flat.

*Type.*—Decorative.

*Diameter across face.*—121 to 127 mm. when fully opened.

B. Corolla of ray florets:

*Color (general tonality from a distance of three meters).*—Dark purple.

*Color.*—Upper surface: 70A to 71B. Under surface: 70D, strongly overlaid with 70B.

*Shape.*—Flat, oblong.

C. Corolla of disc florets:

*Color (mature).*—14B.

*Color (immature).*—14B, overlaid with 144B.

D. Reproductive organs:

*Androecium.*—Present on disc florets only; very few disc florets; moderate pollen.

*Gynoecium.*—Present on both ray and disc florets.

PLANT

A. General appearance:

*Height.*—20 to 30 cm. when grown as a pinched pot mum in a 15 cm. pot with 15 long days after direct sticking of unrooted cuttings and 1 to 3 applications of 2500 ppm B-9 SP.

*Branching pattern.*—Spreading and prolific, with 5 to 6 laterals after pinch.

B. Foliage:

*Color (upper surface).*—147A.

*Color (under surface).*—147B.

*Shape.*—Lobed and slightly serrated (see photograph).

I claim:

1. A new and distinct Chrysanthemum plant named Dark Pomona, as described and illustrated.

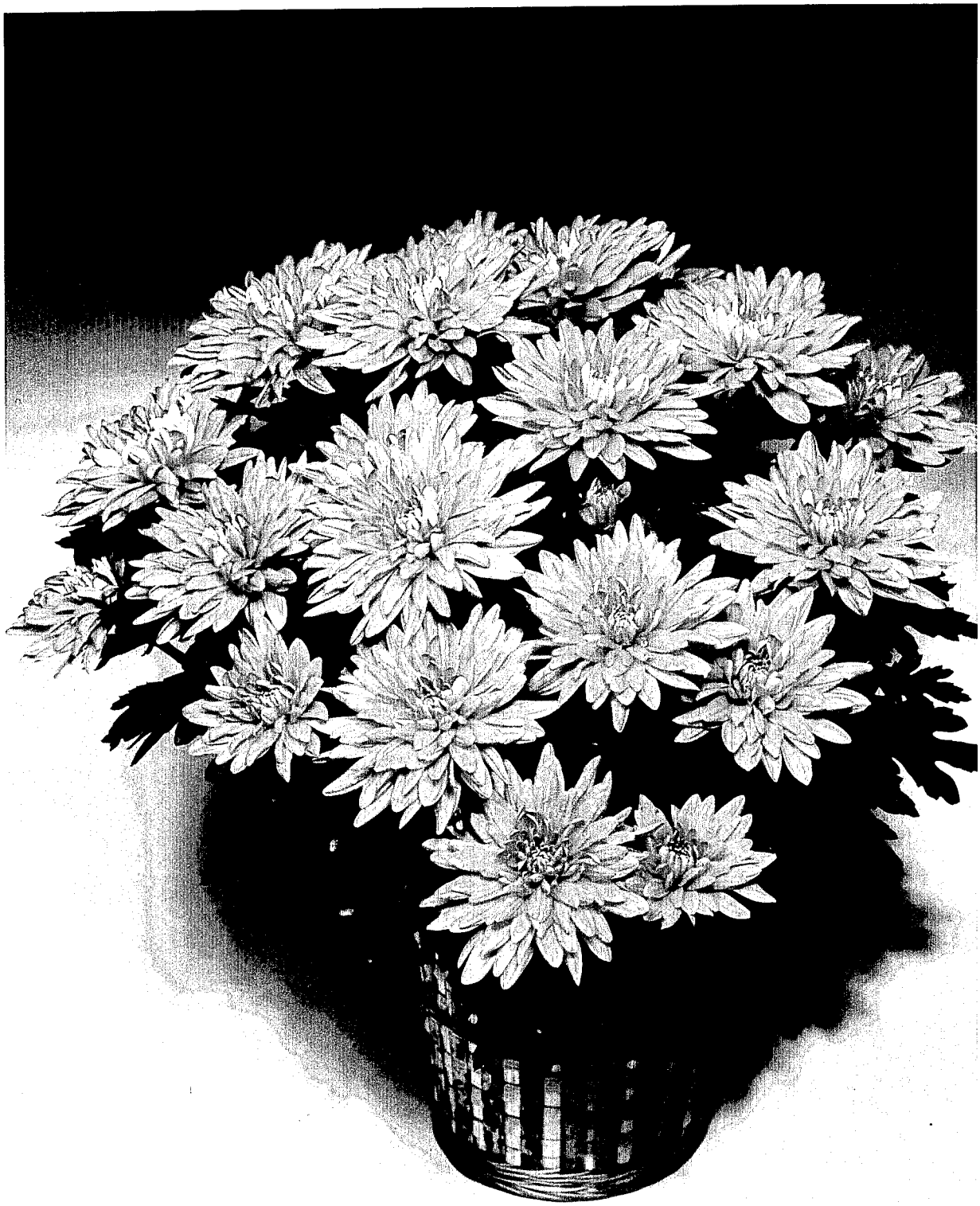

* * * * *